United States Patent [19]

Wessel

[11] Patent Number: 4,885,361
[45] Date of Patent: Dec. 5, 1989

[54] SULFATED OLIGOSACCHARIDES

[75] Inventor: Hans P. Wessel, Heitersheim, Fed. Rep. of Germany

[73] Assignee: Hoffmann-La Roche Inc., Nutley, N.J.

[21] Appl. No.: 221,578

[22] Filed: Jul. 20, 1988

[30] Foreign Application Priority Data

Jul. 31, 1987 [CH] Switzerland ..................... 2938/87

[51] Int. Cl.$^4$ ..................... C07H 11/00; C07H 5/06
[52] U.S. Cl. ..................... 536/118; 536/54
[58] Field of Search ..................... 536/118, 54

[56] References Cited

U.S. PATENT DOCUMENTS 4,273,765  6/1981  Suhara ..................... 536/18

OTHER PUBLICATIONS

K. Yokose et al. (I) J. Antibiotics 36, 1157–65 (1983).
K. Yokose et al., (II) J. Antibiotics, 36, 1166 (1983).
K. Yokose et al. (III) J. Antibiotics, 37, 182–186 (1984).

Primary Examiner—Ronald W. Griffin
Assistant Examiner—Pamela S. Webber
Attorney, Agent, or Firm—Jon S. Saxe; George M. Gould; William H. Epstein

[57] ABSTRACT

Novel compounds with anti-proliferative and mucosa-protective activity are obtained by sulfating trestatins.

4 Claims, 1 Drawing Sheet

SULFATED OLIGOSACCHARIDES

SUMMARY OF THE INVENTION

The present invention is concerned with novel sulfated oligosaccharides of the formula

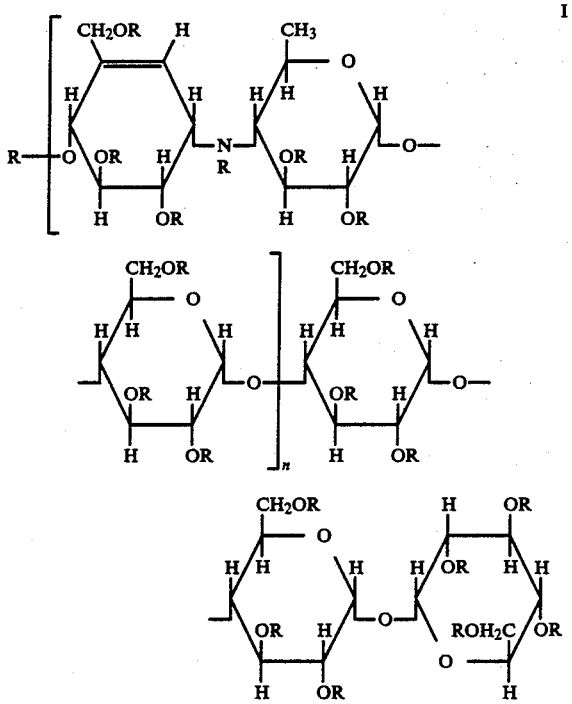

wherein n is a whole number of from 1 to 3; R is hydrogen or a residue —$SO_3M$ and M is a cation; and in which the degree of sulfation is at least 1.

Furthermore, the invention is concerned with a process for the manufacture of the compounds of formula I, their use as medicaments or as active substances for the manufacture of pharmaceutical preparations and pharmaceutical preparations based on the compounds of formula I.

In accordance with this invention it has been found that compounds of formula I inhibit the migration and proliferation of cells of vascular smooth musculature and prevent proliferative arteriosclerotic lesions. Also the compounds exert a less inhibiting effect an blood coagulation than heparin and do not interfere with the growth of endothelial cells. These properties make these compounds useful as a prophylaxis for arteriosclerosis, and especially useful for preventing arteriosclerosis after bypass operations or angioplasty as well as treatment of patients having progressive arteriosclerosis. Furthermore, if has been found that the compounds of formula I have mucosa-protective properties making these useful in the therapy and prophylaxis of gastric ulcers.

DESCRIPTION OF DRAWING

FIG. I is NMR spectrum of the product of Example 1.

DETAILED DESCRIPTION

Figure 1:
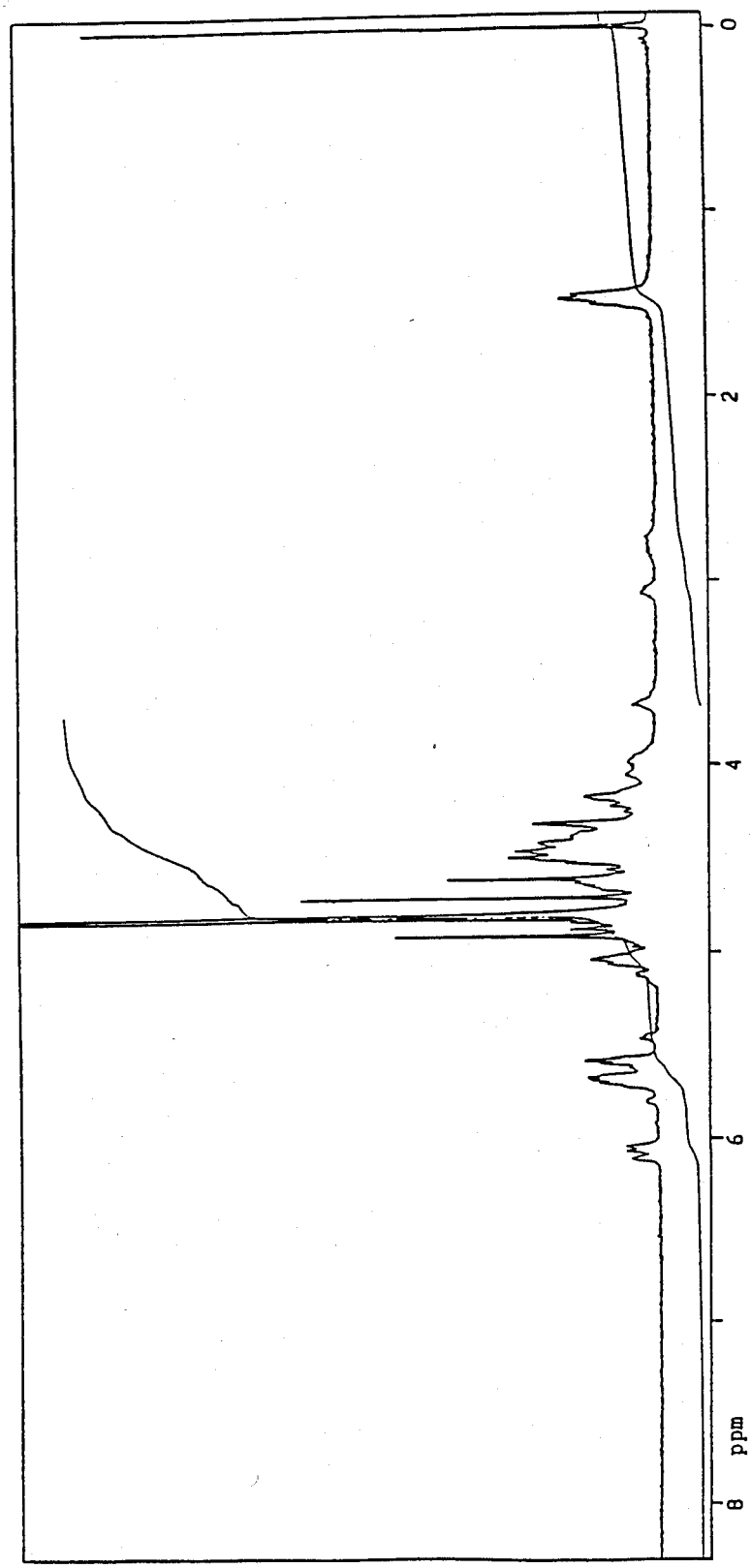

In accordance with this invention, any cation M which is physiologically acceptable can be utilized. Among the physiologically compatible or acceptable cations, e.g. alkali metal cations such as $Na^+$ and $K^+$; ammonium ions and substituted ammonium ions which are derived from tertiary amines such as triethylamine or pyridine or imidazole; or quaternary ammonium ions such as docecyltrimethylammonium, ethylpyridinium and benzethonium; as well as alkaline earth metal cations such as $Ca^{++}$, as preferred. Compounds in which M is $Na^+$ are especially preferred.

The degree of sulfation as used herein designates the average number of —$SO_3M$ residues per unit of each monosaccharide in the compound of formula I. Where n is 1, there are six monosaccharide units in the oligosaccharide of formula I. When n is 2, the compound of formula I contains nine monosaccharide units. Therefore when the degree of sulfation is 1, and n is 1, the compound of formula I contains six —$SO_3M$ units. If the degree of sulfation is 1 and n is 2, the compound of formula I contains nine —$SO_3M$ units. If the degree of sulfation is 2 and n is 1, the compound of formula I contains twelve —$SO_3M$ units. If the degree of sulfation is 2 and n is 2, the compound of formula I contains eighteen —$SO_3M$ units. In accordance with this invention, the highest degree of sulfation for the compound of formula I is about 3.2. In accordance with a preferred embodiment, the degree of sulfation in the compounds of formula I is from about 2 to about 3, with 2.4 being especially preferred.

Of the compounds of formula I those in which n=2 are of particular interest.

The compounds of formula I can be produced in accordance with the invention by treating a compound corresponding to formula I in which all residues R are hydrogen with a sulfating agent.

The starting materials, i.e. non-sulfated compounds corresponding to the compounds of formula I, are known as trestatin A, B and C (see European Patent Specification No. 3616).

The sulfation of trestatin A, B or C in accordance with the present invention can be carried out using methods which are known per se for the sulfation of hydroxy groups.

Examples of sulfating agents which can be used for the manufacture of the compounds of formula I are $SO_3$.complexes such as $SO_3$.pyridine, $SO_3$.trimethylamine, $SO_3$.dioxan and $SO_3$.dimethylformamide. Other examples of sulfating agents are chlorosulfonic acid, mixtures of chlorosulfonic acid and sulfuric acid; and piperidine N-sulfate.

A uniform trestatin (trestatin A, B or C) or a mixture of trestatins can be used as the starting material for the sulfation. The reaction is conveniently effected in a suitable solvent, especially a polar solvent, e.g. dimethylformamide, dimethyl sulfoxide or hexamethylphosphortriamide. The reaction can be carried out at room temperature or a higher temperature, e.g. at 20° C.-70° C., whereby the degree of sulfation can be influenced by variation of the reaction duration and temperature. The degree of sulfation achieved in each case can be assessed by HPLC (high pressure liquid chromatography). The working-up of the reaction mixture and, respectively, the isolation of the reaction product of formula I from the reaction mixture can be effected according to methods known per se, e.g. by gel filtration or ultrafiltration.

The compounds of formula I inhibit the migration and proliferation of cells of the vascular smooth musculature and prevent proliferative arteriosclerotic lesions.

They have less blood coagulation-inhibiting activity than heparin and do not interfere with the growth of endothelial cells. The compounds of formula I can therefore be used for the prophylaxis of arteriosclerosis, especially after bypass operations or angioplasty, as well as for the treatment of patients having progressive arteriosclerosis.

Furthermore, the compounds of formula I exhibit a mucosa-protective activity and can therefore be used for the therapy and prophylaxis of gastric ulcers.

The blood coagulation-inhibiting activity was determined as follows:

aPTT (activated partial thromboplastin time) Test (see Walenga et al., CRC Critical Reviews in Laboratory Sciences 22 (4) 361–389 (1986)): 100 µl of citrated human plasma, which contains various concentrations of test compound, is mixed at 37° C. for 8 minutes with 100µ of Activated Thrombofax (ellagic acid as contact activator and bovine cephalin as platelet lipid substitute). 100 µl of pre-warmed 25 mM calcium chloride solution are then added and the coagultion time is measured in a Fibrometer Coagulation Timer.

anti-Xa Clotting Assay: 25 µl of citrated plasma having various concentrations of test compound are mixed with 75 µl of Factor Xa (the activated blood coagulation factor X) diluted 1:100 with 0.63% citrated buffer (pH 7.3) which contains 41 mM imidazole, 82 mM NaCl and 0.1% albumin. After warming to 37° C. for 2 minutes 200 µl of a 1:1 mixture of Factor X Deficient Plasma and Platelet Substitute are added and the mixture is incubated at 37° C. for 20 seconds. After the addition of 100 µl of prewarmed 50 mM calcium chloride solution the coagulation time is measured in a Fibrometer.

The activity of the test compound is given as the $IC_{50}$ which is the concentration [µg/ml] which leads to a coagulation time which is double the control value.

Inhibition of Thrombin or Factor Xa in the Chromogenic Substrate Assay (Teien et al., Thrombosis Research 10, 399–410 (1977)): The determination was effected in a Cobas-Bio centrifugal automatic spectrophotometer. The buffer solution used consisted of 50 mM Tris buffer, 180 mM NaCl, 7.5 mM EDTA $Na_2$, 1% PEG 6000 (a polyethylene glycol of mol. weight 6000) and 0.02% Tween 80 (a polyoxyethylene sorbitan-monooleate), pH 8.4. The test solution consisted of 50 µl of buffer, 30 µl of anti-thrombin III (1 U/ml), and 20 µl of plasma which contained various concentrations of test compounds. 30 µl of sample solution and 20 µl of water with 180 µl of thrombin were added to the test cuvette in the automatic analyzer. After incubation at 37° C. for 240 seconds 60 µl of the p-nitranilide, H-D-Phe-Pip-Arg-NH.pNA, (0.75 mM in water) and 20 µl of water were added. The liberation of pNA (p-nitroaniline) was followed during 60 seconds at 405 nm in 10 second intervals in comparison to water as the blank. The inhibitory activity is given as the $IC_{50}$ which is the concentration [µg/ml] at which the amidolytic activity of thrombin is reduced by 50% in comparison to the plasma control value.

The inhibition of Factor Xa was measured in the same manner using a solution of Factor Xa (2.8 nkat/ml) and 2 mM of the benzyloxycarbonyl peptide-nitranilide, Bz-CO-Ile-Glu-Arg-NH.pNA, in water in place of thrombin or H-D-Phe-Pip-Arg-NH.pNA.

The results which have been obtained in the experimental procedures described above with the compound of Example 1 and heparin are given hereinafter:

|  | Coagulation inhibition $IC_{50}$ (µg/ml) | | Chromogenic Substrate (amidolytic activity) $IC_{50}$ (µg/ml) | |
|---|---|---|---|---|
|  | aPTT | Xa | IIa | Xa |
| Heparin (standard) | 1.2 | 0.6 | 1.9 | 2.7 |
| Compound of Example 1 | 7 | >30 | >1000 | 550 |

The anti-proliferative activity was determined as follows:

Cells of different origin (Swiss 3T3 mouse fibroblastoid cells, HSMC: human smooth muscle cells and endothelial cells, both isolated from human umbilical cord veins) in RPMI 1640 medium containing 10% calf serum (Swiss 3T3 cells), 15% fetal calf serum (HSMC) or 15% fetal calf serum plus 300 µg/ml of endothelial cell growth supplement (endothelial cells) were cultivated at 37° C. in water-saturated air/5% $Co_2$. Confluent cultures were then washed once with HBSS, removed with 0.05% trypsin/0.02% EDTA and collected by centrifugation. The cells were applied to cell culture plates with a density of 5000 cells/culture and the test compound was added one hour later. The cells were then incubated at 37° C. in air/5% $CO_2$ and collected on the 4th day (Swiss 3T3) and on the 7th day (HSMC and endothelial cells). In order to determine th number of cells, these were washed once with HBSS and adhering cells were incubated for 10 minutes at 37° C. with 0.5 ml of trypsin/EDTA solution for separation. 0.5 ml of formol solution (0.5% paraformaldehyde, 0.145M NaCl, 1.3 mM EDTA) was added to each culture in order to fix the cells. In order to avoid clumping, the cell suspensions were pipetted up and down 20 times. The number of cells was determined with a Coulter counter. The inhibitory action by the test compounds was determined as follows:

$$\% \text{ Inhibition} = \left[ 1 - \frac{\text{Net proliferation with test substance}}{\text{Net proliferation in the control series}} \right] \times 100$$

with the net proliferation being the number of cells at the end of the test minus the number of cells on day 1 (=24 hour after inoculation). The $IC_{50}$ value was extrapolated from the curve of % inhibition against log inhibitor concentration.

The results of this test are given hereinafter:

|  | $IC_{50}$ [µg/ml] | |
|---|---|---|
|  | Swiss 3T3 | HSCM |
| Heparin (standard) | 35 | 45 |
| Compound of Example 1 | 30 | 20 |

The test procedure described hereinafter can be used to determine the mucosa-protective properties:

Oral administration of absolute ethanol to male rats in a dosage of 1 ml per rat leads within 1 hour to bloody lesions of the mucous membrane of the stomach. Various dosages of the substances to be tested (suspended in 0.125% carboxymethylcellulose) or the vehicle alone (control) are administered orally to the rats (1 ml per rat) 30 minutes prior to the treatment with ethanol. One hour after the administration of the ethanol the animals are killed, their stomachs are investigated for the presence of lesions and the number and the total extent of such lesions are determined.

Upon administering 30 mg/kg of the compound of Example 1 the number of lesions was reduced by 28% in comparison to the control group.

In an acute toxicity determination in the mouse the compound of Example 1 was still not lethal after the intravenous application of 500 mg/kg or after the subcutaneous application of 4000 mg/kg.

As mentioned earlier, medicaments containing a compound of formula I are likewise an object of the present invention, as is a process for the manufacture of such medicaments, which comprises bringing one or more compounds of formula I and, if desired, one or more other therapeutically valuable substances into a galenical administration form.

The medicaments can be administered enterally, e.g. orally in the form of tablets, coated tablets, dagrees, hard and soft gelatine capsules, solutions, emulsions or suspensions, or rectally, e.g. in the form of suppositories. However, the administration is preferably effected parenterally, e.g. in the form of injection solutions.

For the manufacture of tablets, coated tablets, dagrees and hard gelatine capsules the active substance can be mixed with pharmaceutically inert, inorganic or organic excipients. As such excipients there can be used for tablets, dagrees and hard gelatine capsules e.g. lactose, maize starch or derivatives thereof, talc, stearic acid or its salts. Suitable excipients for soft gelatine capsules are e.g. vegetable oils, waxes, fats, semi-solid and liquid polyols; depending on the nature of the active substance no excipients are, however, usually required in the case of soft gelatine capsules. For the manufacture of solutions and syrups there are suitable as excipients e.g. water, polyols, saccharose, invert sugar and glucose, for injection solutions there are suitable e.g. water, alcohols, polyols, glycerine and vegetable oils and for suppositories there are suitable e.g. natural or hardened oils, waxes, fats and semi-liquid or liquid polyols.

The pharmaceutical preparations can contain, in addition, preservatives, solubilizers, stabilizers, wetting agents, emulsifiers, sweeteners, colorants, flavorants, salts for varying the osmotic pressure, buffers, coating agents or antioxidants, In the case of enteral administration the resorption of the active substance can be increased with the aid of liposomes.

The dosage of the active substance can vary within wide limits and is, of course, fitted to the individual requirements in each particular case. In general, in the case of parenteral administration a dosage of about 0.1 to 100 mg/kg, preferably of about 1.5 to 15 mg/kg, per day should be appropriate for adults, although the upper limit just given can also be exceeded when this is shown to be indicated.

EXAMPLE 1

Trestatin A (1.0 g, 697 μmol), dried in a high vacuum, was dissolved in dimethylformamide (30 ml) and treated with $SO_3$-pyridine complex (6.8 g, 42.5 mmol). The solution became turbid within a few minutes by the gradual separation of a brownish oil. After stirring for 16 hours the supernatant dimethylformamide solution was decanted off and the residual oil was washed with methanol. An analytical amount of the oil was subjected to gel chromatography on a Sephadex G50 column and the degree of sulfation was determined by NMR spectroscopy (integral comparison of the pyridine and methyl protons). The main amount was treated with 10% sodium acetate solution and evaporated in a vacuum, again dissolved with water and evaporated until all pyridine had been removed. For purification, the resulting trestatin A sulfate sodium salt was chromatographed on Sephadex G50. From the elemental analysis (18.86% S) it is evident that the product has a degree of sulfation $n=2.3$. The NMR spectrum is reproduced in FIG. 1 (internal standard: sodium 2,2,3,3-tetradeutero-3-trimethylsilylpropionate, recorded with Bruker HX-279).

EXAMPLE 2

For the manufacture of an injection solution, 5 mg of the compound of Example 1 and 9 mg of sodium chloride are dissolved in water ad 1 ml. The solution is treated with ascorbic acid (0.5 mg/ml) and benzyl alcohol (0.1 mg/ml) and then filtered sterile.

I claim:

1. Compounds containing a plurality of monosaccharides of the formula

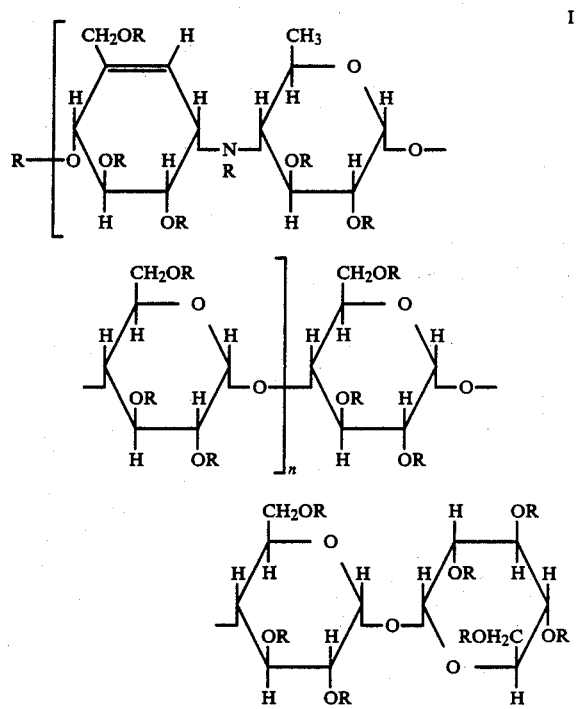

wherein n is a whole number of from 1 to 3; R is hydrogen or a residue $-SO_3M$ and M is a cation; said compounds containing a degree of sulfation per monosaccharide of at least 1.

2. The compounds of claim 1 wherein the degree of sulfation is from 2 to 3.

3. The compounds of claim 1, wherein $n=2$.

4. The compounds of claim 2, wherein the degree of sulfation is about 2.4.

* * * * *